United States Patent [19]
Kimble et al.
[11] Patent Number: 4,595,538
[45] Date of Patent: Jun. 17, 1986

[54] TRI-ALKALI METAL-DI(CARBOXYALKYL)DITHIOCARBAMATE AND TRIAMMONIUM-DI(CARBOXYALKYL)DITHIOCARBAMATE FLOTATION AGENTS

[75] Inventors: Kenneth B. Kimble; Clarence R. Bresson; Harold W. Mark, all of Bartlesville, Okla.

[73] Assignee: Phillips Petroleum Company, Bartlesville, Okla.

[21] Appl. No.: 708,130

[22] Filed: Mar. 4, 1985

[51] Int. Cl.[4] .......................... C07C 155/06; C22B 1/00
[52] U.S. Cl. .......................................... 260/502.56; 75/2; 252/60
[58] Field of Search ....................................... 260/455 A

[56] References Cited

U.S. PATENT DOCUMENTS 3,425,550 2/1969 Baarson et al. ...................... 209/166
3,464,551 9/1969 Falvey .................................. 209/166

*Primary Examiner*—Henry R. Jiles
*Assistant Examiner*—Robert C. Whittenbaugh
*Attorney, Agent, or Firm*—French & Doescher

[57] ABSTRACT

Tri-alkali metal di(carboxyalkyl) dithiocarbamates and triammonium-di(carboxyalkyl) dithiocarbamates which can be characterized by the formula

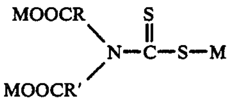

wherein R and R′ can be the same or different and are selected from the group consisting of alkylene radicals, preferably alkylene radicals each preferably having from 1 to 12 carbon atoms, and wherein M is selected from the group consisting of alkali metal atoms and ammonium; their use as ore flotation depressants; and a process for making these novel compositions are disclosed.

10 Claims, No Drawings

TRI-ALKALI METAL-DI(CARBOXYALKYL)DITHIOCARBAMATE AND TRIAMMONIUM-DI(CARBOXYALKYL)DITHIOCARBAMATE FLOTATION AGENTS

This invention relates generally to novel chemical compositions. In one aspect, the invention relates to a process for making such compositions. In another aspect, the invention relates to ore flotation processes employing such novel compositions.

Froth flotation is a process for recovering and concentrating minerals from ores. In a froth flotation process, the ore is crushed and wet ground to obtain a pulp. Additives such as mineral flotation or collecting agents, frothing agents, suppressants or depressants, stabilizers, etc., are added to the pulp to assist separating valuable minerals from the undesired or gangue portions of the ore in subsequent flotation steps. The pulp is then aerated to produce a froth at the surface. The minerals which adhere to the bubbles or froth are skimmed or otherwise removed and separated. The froth product or the reject product or both can then be further processed to obtain the desired minerals. Typical mineral flotation collectors include xanthates, amines, alkyl sulfates, arenes, sulfonates, dithiocarbamates, dithiophosphates, and thiols.

It is known from the art that some dithiocarbamates are useful as collecting agents. U.S. Pat. No. 3,464,551, for instance, describes dialkyl dithiocarbamates and the production thereof. U.S. Pat. No. 3,425,550 describes dialkyl dithiocarbamates and their production as well as the utility of these compounds as flotation collectors.

It is a continuing goal in the ore-processing industry to increase the productivity of ore flotation processes and, above all, to provide specific procedures which are selective to one ore or metal over other ores or metals present in the treated material.

It is an object of this invention to provide new dithiocarbamates.

A further object of this invention is to provide a process for making such dithiocarbamates.

Yet another object of this invention is to provide an ore flotation process wherein such new dithiocarbamates are used as flotation agents.

These and other objects, advantages, details, features and embodiments of this invention will become apparent to those skilled in the art from the following detailed description of the invention and the appended claims.

In accordance with this invention it has now been found that tri-alkali metal-di(carboxyalkyl)dithiocarbamate and tri-ammonium-di(carboxyalkyl)dithiocarbamate salts are very effective as depressants in ore flotation processes.

Thus, in accordance with a first embodiment of this invention, novel compositions of matter are provided which can be characterized by the formula

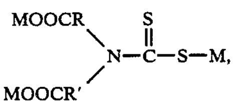

(I)

wherein R and R′ are each selected from the group consisting of alkylene radicals, preferably alkylene radicals each having from 1 to 12 carbon atoms and more preferably each having from 1 to 4 carbon atoms; and wherein M is selected from the group consisting of alkali metal atoms and ammonium, preferably sodium. The alkylene radicals R and R′ can be the same or different.

In accordance with a second embodiment of the invention there is provided a process for producing the above-defined novel dithiocarbamates. This process comprises reacting an aqueous alkali metal hydroxide, wherein the alkali metal is preferably selected from the group consisting of Li, Na, Cs, Rb and K, or aqueous ammonium hydroxide with an imino dialkanoic acid, preferably an imino dialkanoic acid characterized by the formula

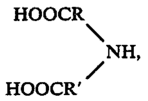

(II)

wherein R and R′ are each selected from the group consisting of alkylene radicals, preferably alkylene radicals each having from 1 to 12 carbon atoms and more preferably each having from 1 to 4 carbon atoms, and $CS_2$ to form a dithiocarbamate having the formula (I); and recovering the product of formula (I) as the product of the process.

The imino dialkanoic acids useful to produce the novel dithiocarbamates of the present invention include, for example, but are not limited to such materials as iminodiacetic acid, iminodipropionic acid, iminodibutanoic acid and the like. The alkylene radicals R and R′ can be the same or different.

The detailed operating conditions for the individual steps are not critical and specific values for the steps can be seen from the following examples.

The separation of the product of formula (I) is carried out by standard techniques.

A further embodiment of this invention resides in an ore flotation process. More specifically, such further embodiment of this invention resides in a process for separating valuable ore materials from gangue materials. The ore flotation process of this invention distinguishes over the known ore flotation processes primarily in the employment of a new flotation agent to be defined. Otherwise the recovery process involves crushing of the ore and ore grinding to obtain a pulp. In this pulp the flotation agent is incorporated and the pulp is aerated to produce a froth at the surface which is rich in valuable ore materials but depleted of the gangue materials or vice versa. The ore materials, optionally, after additional flotation and frothing steps, are recovered. Frothing agents, selective depressants and stabilizers which are well known in the art can be used in the various steps.

The tri-alkali metal-di(carboxyalkyl)dithiocarbamates and tri-ammonium-di(carboxyalkyl)dithiocarbamates useful in the ore flotation process of this invention are characterized by the formula

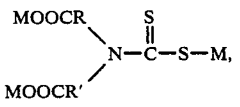

(I)

wherein R and R′ are each selected from the group consisting of alkylene radicals, preferably alkylene radicals each having from 1 to 12 and more preferably each having from 1 to 4 carbon atoms, and M is selected from the group consisting of alkali metal atoms and ammonium. The alkylene radicals R and R′ can be the same or different. Examples of such compounds useful as suppressants or depressants in the process of this invention are those generally characterized as tri-alkali metal N,N-di(carboxyalkyl)dithiocarbamates, such as for example:

trisodium N,N-bis(carboxymethyl)dithiocarbamate,
trisodium N,N-bis(2-carboxyethyl)dithiocarbamate,
trisodium N,N-bis(3-carboxypropyl)dithiocarbamate,
trisodium N,N-bis(4-carboxybutyl)dithiocarbamate,
tripotassium N,N-bis(carboxymethyl)dithiocarbamate,
tripotassium N,N-bis(2-carboxyethyl)dithiocarbamate,
tripotassium N,N-bis(3-carboxypropyl)dithiocarbamate,
tripotassium N,N-bis(4-carboxybutyl)dithiocarbamate,
trilithium N,N-bis(carboxymethyl)dithiocarbamate,
trilithium N,N-bis(2-carboxyethyl)dithiocarbamate,
trilithium N,N-bis(3-carboxypropyl)dithiocarbamate,
trilithium N,N-bis(4-carboxybutyl)dithiocarbamate and those generally characterized as triammonium N,N-di(carboxyalkyl)dithiocarbamates, such as, for example:

triammonium N,N-bis(carboxymethyl)dithiocarbamate,
triammonium N,N-bis(2-carboxyethyl)dithiocarbamate,
triammonium N,N-bis(3-carboxypropyl)dithiocarbamate,
triammonium N,N-bis(4-carboxybutyl)dithiocarbamate and the like, and combinations of any two or more thereof.

It will be understood that the designation N,N in the nomenclature of various di(carboxyalkyl)dithiocarbamates and bis(carboxyalkyl)dithiocarbamates herein disclosed may be omitted for convenience, but it will be understood that the dithiocarbamates so disclosed are those having the N,N-substitution.

The presently preferred composition used as the ore flotation depressant in the process of this invention is trisodium N,N-(carboxymethyl)dithiocarbamate.

The amount of tri-alkali metal-di(carboxyalkyl)dithiocarbamate or triammonium-di(carboxyalkyl)dithiocarbamate employed in the process of this invention is not critical. The quantity will depend upon whether it is being used with an ore or a concentrate and whether there is a large or small amount of mineral to be depressed. Generally, the amount of tri-alkali metal-di(carboxyalkyl)dithiocarbamate or triammonium-di(carboxyalkyl)dithiocarbamate employed in the process will be in the range of from about 0.1 lb to about 10 lb of the inventive depressant per ton of solids (lb/ton). Preferably the inventive ore flotation depressant will be used in a quantity in the range from about 0.15 to about 6 lb/ton of solids.

It is generally believed that the tri-alkali metal-di(carboxyalkyl)dithiocarbamates and triammonium-di(carboxyalkyl)dithiocarbamates disclosed herein are useful for suppressing or depressing the flotation of certain metal sulfide minerals during ore flotation processes. It is also understood that the tri-alkali metal-di(carboxyalkyl)dithiocarbamates and triammonium-di(carboxyalkyl)dithiocarbamates may suppress a mixture of metals or minerals that are contained in a particular mining deposit or ore, said mixture being further separated by subsequent froth flotations or any other conventional separating methods. The tri-alkali metal-di(carboxyalkyl)dithiocarbamates and triammonium-di(carboxyalkyl)dithiocarbamates herein disclosed are particularly useful for suppressing or depressing minerals based on copper, nickel, iron, lead and zinc from the total ore. Examples of such minerals include, but are not limited to such materials as

| | |
|---|---|
| Molybdenum-bearing ores: | |
| Molybdenite | $MoS_2$ |
| Wulfenite | $PbMoO_4$ |
| Powellite | $Ca(Mo_1W)O_4$ |
| Ferrimolybdite | $Fe_2MO_3O_{12}.8H_2O$ |
| Copper-bearing ores: | |
| Covellite | $CuS$ |
| Chalcocite | $Cu_2S$ |
| Chalcopyrite | $CuFeS_2$ |
| Bornite | $Cu_5FeS_4$ |
| Cubanite | $Cu_2SFe_4S_5$ |
| Valerite | $Cu_2Fe_4S_7$ or $Cu_3Fe_4S_7$ |
| Enargite | $Cu_3(As,Sb)S_4$ |
| Tetrahedrite | $Cu_{12}Sb_4S_{13}$ |
| Tennanite | $Cu_{12}As_4S_{13}$ |
| Cuprite | $Cu_2O$ |
| Tenorite | $CuO$ |
| Malachite | $Cu_2(OH)_2CO_3$ |
| Azurite | $Cu_3(OH)_2CO_3$ |
| Antlerite | $Cu_3SO_4(OH)_4$ |
| Brochantite | $Cu_4(OH)_6SO_4$ |
| Atacamite | $Cu_2Cl(OH)_3$ |
| Chrysocolla | $CuSiO_3$ |
| Famatinite | $Cu_3(Sb,As)S_4$ |
| Bournonite | $PbCuSbS_3$ |
| Lead-Bearing ore: | |
| Galena | $PbS$ |
| Zinc-Bearing ores: | |
| Sphalerite | $ZnS$ |
| Zincite | $ZnO$ |
| Smithsonite | $ZnCO_3$ |
| Chromium-Bearing ores: | |
| Daubreelite | $FeSCrS_3$ |
| Chromite | $FeO.Cr\ Cr_2O_3$ |
| Iron-Bearing ores: | |
| Pyrite | $FeS_2$ |
| Marcasite | $FeS_2$ |
| Pyrrhotite | $Fe_7S_8$ |
| Nickel-Bearing ores: | |
| Pentlandite | (FeNi)S |
| Millerite | $NiS$ |
| Niccolite | $NiAs$ |

The presently preferred ores in connection with which the process of this invention is applied are molybdenum, copper, lead, nickel and iron ores or minerals.

Separation Conditions

Any froth flotation apparatus can be used in this invention. The most commonly used commercial flotation machines are the Agitar (Galigher Co.), Denver Sub-A (Denver Equipment Co.), and the Fagergren (Western Machinery Co.). Smaller laboratory scale apparatus such as the Hallimond cell can also be used.

The instant invention was demonstrated in tests conducted at ambient room temperature to about 37° C. (100° F.) and atmospheric pressure. However, any temperature or pressure generally employed by those skilled in the art is within the scope of this invention.

The following examples serve to illustrate this invention without undue limitation of the scope thereof.

EXAMPLE I

This example describes the preparation of trisodium N,N-bis(carboxymethyl)dithiocarbamate, a novel compound. To a one liter 3-neck flask fitted with a stirrer, reflux condenser, thermometer and dropping funnel was added 352 grams of distilled water and 126 grams (3.15 moles) of sodium hydroxide. After the sodium hydroxide had dissolved there was slowly added with stirring 133.1 grams (1.0 mole) of iminodiacetic acid. After cooling in a wet ice bath to about 25° C., carbon disulfide (76.1 grams, 1.0 mole) was added very slowly partly because the acid salt had come out of solution. As the carbon disulfide reacted, the reactants went back into solution resulting in an amber colored liquid. The reaction product mixture was considered to be a 40 percent aqueous solution of trisodium N,N-bis(carboxymethyl)dithiocarbamate.

EXAMPLE II

This example describes the procedure used to evaluate the reaction product mixture prepared in Example I as a depressant in a Mo ore flotation process wherein Cu and Fe sulfide minerals are depressed while Mo continues to be floated. About 1000 grams of a Mo/Cu/Fe-containing ore (Moly Corp. Questa Mine) along with 660 milliliters of water, 0.1 milliliter (0.2 lb/ton) diesel oil (Mo collector) and 14 drops (0.1 lb/ton) frother (6:3 weight ratio of methyl isobutylcarbinol:pine oil) were ground in a table ball mill for 6 minutes 42 seconds and transferred to a 2.5 liter capacity Wemco flotation cell, conditioned 30 seconds at 1500 rpm and floated for 8 minutes. The concentrate at this point is referred to as the rougher concentrate. The rougher concentrate was transferred to a 1.6 liter capacity Denver flotation cell along with enough water to bring the level of slurry to within 1 or 2 inches of the cell lip. To the cell was added 0.93 milliliters (5 lbs/ton) of the inventive depressant along with enough lime to maintain a pH of 8.5. The slurry was conditioned for 2 minutes at 1100 rpm whereupon 1 drop (about 0.007 lb/ton) diesel oil Mo collector and 2 drops (about 0.014 lb/ton) frother was further added. The slurry was conditioned for 30 seconds and floated for 4 minutes. This second float, referred to as the cleaner concentrate, was filtered, dried and analyzed. The procedure was repeated and an average weight percent recovery calculated based on the amount of Mo, Cu, and Fe present in the rougher concentrate. In this manner there was obtained average weight percent recoveries of 73.0 percent Mo, 35.9 percent Cu, and 6.7 percent Fe for the inventive depressant.

The procedure was then repeated several times using a known commercial depressant and a control where no depressant was added. These results are listed in Table I where it can be seen that the inventive trisodium N,N-bis(carboxymethyl)dithiocarbamate depresses the flotation of Cu and Fe while not greatly interfering with the flotation of Mo when compared with runs 1 and 2 where no depressant was employed. Compared with a known depressant (runs 3 and 4), the inventive depressant gives a significantly higher Mo recovery (indicating less inteference) but also a higher recovery of Cu and Fe.

TABLE I

Trisodium N,N—Bis(Carboxymethyl) Dithiocarbamate as a Mineral Depressant in Ore Flotation

| Run | Depressant, 5 lb/ton solids | | Wt. % Recovery MO | Cu | Fe |
|---|---|---|---|---|---|
| Control: | | | | | |
| 1 | No additive | | 78.5 | 70.3 | 12.7 |
| 2 | No additive | | 75.8 | 62.0 | 6.4 |
| | | Avg. = | 77.2 | 66.2 | 9.6 |
| 3 | $Na_2$—Carboxymethyl Trithiocarbamate[a] | | 48.5 | 4.7 | 3.3 |
| 4. | $Na_2$—Carboxymethyl Trithiocarbamate[a] | | 51.3 | 6.2 | 2.5 |
| | | Avg. = | 49.9 | 5.5 | 2.9 |
| Invention: | | | | | |
| 5 | $Na_3$—N,N—Bis(carboxymethyl)Dithiocarbamate | | 78.9 | 43.5 | 7.3 |
| 6 | $Na_3$—N,N—Bis(carboxymethyl)Dithiocarbamate | | 67.5 | 28.3 | 6.1 |
| | | Avg. = | 73.0 | 35.9 | 6.7 |

S
‖
[a]$NaOOCCH_2$—S—C—S—Na, 40% aq. sol'n

EXAMPLE III

This example describes the procedure used for further evaluation of the reaction product mixture prepared in Example I as a depressant in a Mo flotation process wherein Cu, Pb and Fe sulfide minerals are depressed while Mo continues to be floated. About 1000 grams of a Mo/Cu/Pb/Fe-containing ore (Moly Corp. Questa Mine) along with 660 milliliters of water, 0.1 milliliter (0.2 lb/ton) diesel oil (Mo collector) and 14 drops (0.1 lb/ton) frother (6:3 weight ratio of methyl isobutylcarbinol:pine oil) were ground in a table ball mill for 6 minutes 42 seconds and transferred to a 2.5 liter capacity Wemco flotation cell, conditioned about 30 seconds at 1500 rpm and floated for about 8 minutes. The concentrate produced at this point is referred to as the rougher concentrate. The rougher concentrate was transferred to a 1.6 liter capacity Denver D-12 flotation cell along with enough water to bring the level of slurry to within 1 or 2 inches of the cell lip. In each of the inventive runs 7–14 a quantity of the inventive depressant was added to the cell with sufficient aqueous NaOH to maintain a pH of about 8.5. In each of the runs 9–14 the slurry was conditioned for 2 minutes at 1100 rpm whereupon 1 drop (about 0.007 lb/ton) diesel oil (Mo collector) and 2 drops (about 0.014 lb/ton) frother was further added. The slurry was conditioned for 30 seconds and floated for 4 minutes. This second float produced a cleaner concentrate which was filtered, dried and analyzed. In each run the weight percent recovery of Mo, Cu, Pb and Fe was calculated based on the corresponding amounts of Mo, Cu, Pb and Fe present in the rougher concentrate. The average weight percent recovery for the two runs for each depressant dosage and for the two control runs without depressant were also calculated. These results are listed in Table II where it can be seen that the inventive trisodium N,N-bis(carboxymethyl)dithiocarbamate selectively depresses the flotation of Cu, Pb and Fe (runs 9–14) while substantially maintaining the flotation of Mo when compared with control runs 7 and 8 where no depressant was employed. It is significant to note that the average weight percent recovery of Mo at an inventive depressant dosage of 0.4 lb/ton solids (runs 9 and 10) and at an inventive depressant dosage of 0.8 lb/ton solids (runs 11 and 12) was actually slightly increased over the average weight percent recovery of Mo in control runs 7 and 8 employing no depressant.

TABLE II

Trisodium N,N—Bis(Carboxymethyl) Dithiocarbamate as a Mineral Depressant in Ore Flotation

| | | Depressant Dosage | | Wt. % Recovery | | | |
|---|---|---|---|---|---|---|---|
| Run | Depressant | ml | lb/ton solids | Mo | Cu | Pb | Fe |
| Control: | | | | | | | |
| 7 | No additive | — | — | 89.47 | 75.01 | 73.32 | 12.11 |
| 8 | No additive | — | — | 86.02 | 77.63 | 75.37 | 10.52 |
| Avg. | | | | 87.75 | 76.32 | 74.35 | 11.32 |
| Invention: | | | | | | | |
| 9 | TNNBD[(a)] | 1 | 0.4 | 87.43 | 42.38 | 33.68 | 10.09 |
| 10 | (a) | 1 | 0.4 | 89.22 | 51.34 | 53.09 | 11.66 |
| Avg. | | | | 88.33 | 46.86 | 43.39 | 10.88 |
| 11 | (a) | 2 | 0.8 | 87.64 | 29.09 | 57.20 | 9.47 |
| 12 | (a) | 2 | 0.8 | 88.66 | 36.61 | 44.66 | 9.29 |
| Avg. | | | | 88.15 | 32.85 | 50.93 | 9.38 |
| 13 | (a) | 4 | 1.6 | 87.68 | 31.19 | 50.00 | 9.35 |
| 14 | (a) | 4 | 1.6 | 85.17 | 34.60 | 48.09 | 8.56 |
| Avg. | | | | 86.43 | 32.90 | 49.05 | 8.96 |

[(a)]Trisodium N,N—bis(carboxymethyl) dithiocarbamate

In summary, the data herein disclosed reveal that the novel tri-alkali metal-di(carboxyalkyl)dithiocarbamates and triammonium-di(carboxyalkyl)dithiocarbamates of the present invention are useful as depressants in ore flotation processes. The novel compounds are shown to be particularly suited for suppressing Cu, Fe, and Pb in the flotation of Mo.

Reasonable variations and modifications which will become apparent to those skilled in the art can be made in this invention without departing from the spirit and scope thereof.

We claim:

1. The composition represented by the formula

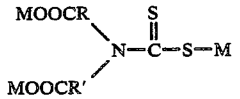

wherein R and R′ are each selected from the group consisting of alkylene radicals each having from 1 to 12 carbon atoms and can be the same or different; and wherein M is selected from the group consisting of alkali metal atoms and ammonium.

2. A composition in accordance with claim 1 wherein R and R′ are each selected from the group consisting of alkylene radicals each having from 1 to 4 carbon atoms.

3. A composition in accordance with claim 1 wherein R and R′ are methylene radicals.

4. A composition in accordance with claim 1 wherein M is a sodium atom.

5. Tri-alkali metal-di(carboxyalkyl)dithiocarbamate selected from the group consisting of:

trisodium N,N-bis(carboxymethyl)dithiocarbamate,
trisodium N,N-bis(2-carboxyethyl)dithiocarbamate,
trisodium N,N-bis(3-carboxypropyl)dithiocarbamate,
trisodium N,N-bis(4-carboxybutyl)dithiocarbamate,
tripotassium N,N-bis(carboxymethyl)dithiocarbamate,
tripotassium N,N-bis(2-carboxyethyl)dithiocarbamate,
tripotassium N,N-bis(3-carboxypropyl)dithiocarbamate,
tripotassium N,N-bis(4-carboxybutyl)dithiocarbamate,
trilithium N,N-bis(carboxymethyl)dithiocarbamate,
trilithium N,N-bis(2-carboxyethyl)dithiocarbamate,
trilithium N,N-bis(3-carboxypropyl)dithiocarbamate,
trilithium N,N-bis(4-carboxybutyl)dithiocarbamate.

6. Tri-alkali metal-di(carboxyalkyl)dithiocarbamate wherein each alkylene radical has from 1 to 12 carbon atoms.

7. Tri-alkali metal-di(carboxyalkyl)dithiocarbamate in accordance with claim 6 wherein each alkylene radical has from 1 to 4 carbon atoms.

8. Triammonium-di(carboxyalkyl)dithiocarbamate wherein each alkylene radical has from 1 to 12 carbon atoms.

9. Triammonium-di(carboxyalkyl)dithiocarbamate in accordance with claim 8 wherein each alkylene radical has from 1 to 4 carbon atoms.

10. Triammonium-di(carboxyalkyl)dithiocarbamate selected from the group consisting of:

triammonium N,N-bis(carboxymethyl)dithiocarbamate,
triammonium N,N-bis(2-carboxyethyl)dithiocarbamate,
triammonium N,N-bis(3-carboxypropyl)dithiocarbamate,
triammonium N,N-bis(4-carboxybutyl)dithiocarbamate.

* * * * *